United States Patent [19]

Daniel et al.

[11] Patent Number: 4,963,128
[45] Date of Patent: Oct. 16, 1990

[54] CHEST TUBE AND CATHETER GRID FOR INTRATHORACIC AFTERLOAD RADIOTHERAPY

[75] Inventors: Thomas M. Daniel; Seung S. Hahn, both of Charlottesville, Va.

[73] Assignee: University of Virginia Alumni Patents Foundation, Charlottesville, Va.

[21] Appl. No.: 326,733

[22] Filed: Mar. 21, 1989

[51] Int. Cl.$^5$ .............................................. A61M 36/12
[52] U.S. Cl. ..................................... 600/7; 128/657; 128/658; 604/93; 604/280
[58] Field of Search ............... 600/3, 7; 128/657, 658; 604/93, 280

[56] References Cited

U.S. PATENT DOCUMENTS 4,706,652 11/1987 Horowitz ............................... 600/7

Primary Examiner—Max Hindenburg
Assistant Examiner—Kevin Pontius
Attorney, Agent, or Firm—James Creighton Wray

[57] ABSTRACT

An apparatus and method for intraoperative internal placement of an afterloading catheter tube grid for postoperative radiotherapy using a semi-rigid tube having inserted within a plurality of catheters which extends outwardly from the distal end of the semi-rigid tube for a predetermined distance and attaching these distally outward extending catheter tubes to a soft sheet so that the catheter tube maintain a parallel position to one another over the predetermined distance. The proximal ends of these catheter tubes extend outwardly from the proximal end of the semi-rigid tube and are located on the outside of the body. These proximal ends of the catheters are left open for loading of the radioactive material into these catheter tubes, while the distal ends are closed to prevent airleak and to stop the radioactive material. The soft sheet is provided with eyelets at each of the four corners, and these eyelets are used to secure the soft sheet with sutures to the inside of the cavity wall over the area intended for radiation therapy. A stiff cover cap is provided so as to cover the furled soft sheet, and this cover cap attaches to the distal end of the semi-rigid tube. This cover cap is removed when the present invention is inserted into the body cavity.

9 Claims, 1 Drawing Sheet

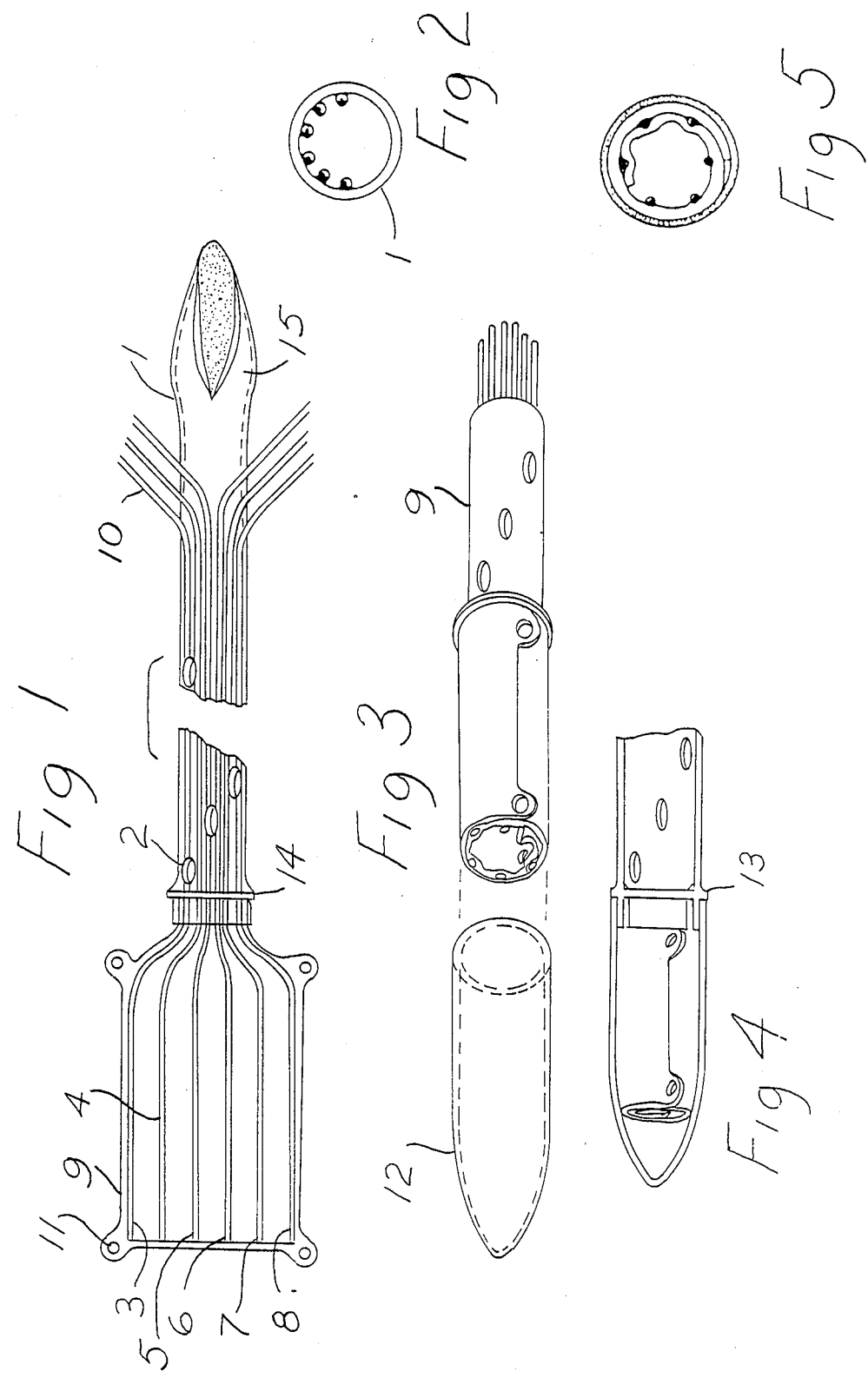

CHEST TUBE AND CATHETER GRID FOR INTRATHORACIC AFTERLOAD RADIOTHERAPY

BACKGROUND OF THE INVENTION

1. Field of the Invention

This invention relates to a novel method for intraoperative placement of afterloading catheters for postoperative radiotherapy.

2. Prior Art

The role of local radiation therapy, also known as brachytherapy, is supplemental to external beam radiation therapy. External beam radiation therapy is largely limited by tolerance of normal tissues such as the spinal cord, lungs, heart, skin, soft tissue, and bones in the treated area. When brachytherapy is used in conjunction with external beam therapy, a tumor bed dose can be safely boosted up to 8,000 rads.

In a report by McCaughan, 54 patients with chest wall invasion by non-oat cell carcinoma of the lung were examined (McCaughan et al., "Chest Wall Invasion in Carcinoma of the Lung", J. THORAC CARDIOVASC SURG, 89:836–841 (1985)). Six of the 54 patients had microscopic disease at the surgical margin without gross residual tumor. Three of these patients received external beam radiation and three did not. One patient in each group developed a local recurrence. Recognition of the limitations of surgical resection and conventional external beam radiation therapy in preventing local recurrence and its failure to improve survival has led to trials of perioperative brachytherapy. The technique for delivering thoracic brachytherapy was originally developed by Henschke and most recently described by Kitagawa (Henschke et al., "Interstitial Implantation of Radioactive Seeds During Thoracotomy", *Lung Cancer, a Study of Five Thousand Memorial Hospital Cases*, 323–346 (C.V. Mosby Co. 1968); and Kitagawa et al., "Afterloading Technique for Interstitial Irradiation of Lesions in Deep-Seated Organs", RADIOLOGY 143:543–547 (1982)). Hilaris in a pilot study of 88 patients utilized permanent Iodine-125 implantation for the unresectable primary lung lesion, temporary mediastinal Iridium-192 implantation via afterloading catheters, and post-operative external beam radiation (Hilaris et al., "Intraoperative Radiotherapy in Stage I and II Lung Cancer", SEM SURG ONC 3:22–32 (1987)). Mediastinal and local regional control was observed in 76% of the 88 patients at a twenty-six month median follow-up. He suggested that combined external beam therapy and local therapy of 6,000 rads or more would control 60–75% of the bulky tumor and 85% of patients with microscopic residual.

In the past, the placement of the small individual afterloading catheters used in thoracic brachytherapy required a time-consuming process of multiple chest wall punctures through areas of the chest wall poorly accessible when the patient lay in the lateral decubitus position. Also there is limitation of access to the thoracic cavity and mediastinum because of the displacement by the expanding and contracting lung and rib cage movement. The standard technique of directly inserting 17 gauge afterloading catheters is particularly limited by later crimping when the catheters are inserted at more lateral sites to achieve chest wall brachytherapy as opposed to treatment of the more fixed mediastinal strictures as described by Hilaris. When crimping does occur, it often prevents subsequent delivery of the radioactive source.

SUMMARY OF THE INVENTION

The stented afterloading catheter and method of installation as described in this application overcome the disadvantages found in the prior art. The present invention provides many specific advantages over the prior art. First, it can be rapidly instituted during surgery through a routinely-placed chest tube or other semi-rigid drainage tube when unexpected tumor invasion is discovered without requiring prior coordination with a radiation oncologist. The materials required are available in standard operating theaters and radiotherapy departments. Second, it can be positioned anywhere against the chest wall and is not limited to mediastinal placement. Third, it avoids crimping of the small 17 gauge catheters at the chest wall or other cavity wall exit site during the post-operative period, and fourth, it produces a relatively fixed plane for local technique and also avoids exposure of the operating room personnel to radioactive sources while still permitting the use of post-operative radiotherapy or brachytherapy. The present invention may also be used in cases where microscopic residual tumor may be present following a pulmonary resection and where extensive removal of the chest wall or mediastinal structures is thought to be contraindicated or impossible. The invention may also be employed in the treatment of intra-abdominal and pelvic neoplasms.

These and other and further objects and features of the invention are apparent in the disclosure, which includes the above and ongoing specification with the claims and the drawings.

BRIEF DESCRIPTION OF THE DRAWINGS

FIG. 1 shows the preferred embodiment of the present invention in its open or unfurled position.

FIG. 2 shows a cross-section of the present invention illustrating the position of the catheter tubes inside the chest tube when the invention is in its open position.

FIG. 3 shows the present invention in its closed position with the cover cap removed.

FIG. 4 illustrates the present invention with the cover cap being in place.

FIG. 5 shows a cross-section of the present invention in its closed position.

DETAILED DESCRIPTION OF THE DRAWINGS

Referring to FIG. 1, the present invention comprises a standard chest tube 1 with drainage holes 2. The preferred chest tube is a No. 32 Fr. chest tube which comes in a standard length. Within this chest tube are attached the 17-gauge afterloading catheters 3–8. Preferably, six catheter tubes are used in the present invention. These catheters emerge from the distal end 14 of chest tube 1 and are attached to a soft sheet 9. Preferably this soft sheet is made of plastic. In FIG. 1, this soft sheet 9 is shown in its open or unfurled position with the catheter tubes 3–8 molded to this soft sheet at constant parallel positions. Preferably, these catheter tubes are spaced 1 cm. apart and cover a grid area 5 cm. wide and 6 cm. long. The catheter tubes 3–8 have closed distal ends to prevent air leak and to hold the radioactive material. These catheter tubes are preferably made of polyethylene. The proximal other ends of the catheter tubes 3–8 extend outwardly from holes 10 in the proximal end 15 of the chest tube 1. These ends of the catheter tubes are opened and allow for loading of the radioactive material into these catheter tubes.

In FIG. 1, the soft sheet 9 is provided with eyelets 11 at each of its four corners. The eyelets 11 are used to secure this sheet with catheter tubes with sutures (not shown) to the inside of the chest wall over the area intended for radiation therapy.

FIG. 2 shows a cross-section of the chest tube 1 and illustrates the positioning of the catheter tubes 3–8 inside the chest tube 1 when the soft sheet 9 is in its open position.

FIG. 3 illustrates the soft sheet 9 in its furled position. This furled soft sheet is then covered by a stiff cover cap 12, which is used to protect the furled soft sheet and catheter tubes when inserting the chest tube 1 from outside of the chest wall at the time of the surgery. Preferably the cover cap is made of plastic. The cover cap 12 is to be removed once the tip of the tube is in the thoracic or other body cavity.

FIG. 4 shows the present invention, again in its furled position with the cover cap 12 on the present invention. As can be seen in FIG. 4, the chest tube 1 is provided with a tapered flange 13 to prevent the cover cap 12 from being dislodged during tube insertion.

FIG. 5 shows a cross-section of the chest tube and the positioning of the catheter tubes 3–8 located inside the chest tube when the soft sheet 9 is in its furled position.

While the invention has been described with reference to specific embodiments, modifications and variations may be made without departing from the scope of the invention, which is defined in the following claims.

We claim:

1. An apparatus for internal radiation therapy, comprising:
    a semi-rigid tube having a distal and proximal end, wherein the distal end is inserted into a body cavity, while the proximal end remains outside of the body;
    a plurality of catheters having closed distal ends and open proximal ends, wherein the catheters are inserted into the semi-rigid tube so that the distal ends of the catheters extend outwardly from the distal end of the semi-rigid tube for a predetermined distance, and wherein the open proximal ends of the catheters extend outwardly from the proximal end of the semi-rigid tube and are located on the outside of the body; and
    a soft sheet to which the distal ends of the catheter tubes are attached so that the catheter tubes maintain a parallel position to one another over the predetermined distance,
    wherein the semi-rigid tube has a diameter of sufficient size so that when the catheters are inserted into the semi-rigid tube, the semi-rigid tube is capable of performing as a drainage tube.

2. The apparatus of claim 1, wherein the soft sheet is provided with eyelets so that the soft sheet may be secured with sutures to an area intended for radiation therapy.

3. The apparatus of claim 1, further comprising a stiff cover cap which covers the furled soft sheet and attaches to the distal end of the semi-rigid tube.

4. The apparatus of claim 3, wherein the semi-rigid tube is further provided with a tapered flange to prevent dislodgement of the stiff cover cap during the tube insertion into the body cavity.

5. The apparatus of claim 1, wherein the semi-rigid tube is a chest tube with drainage holes.

6. The apparatus of claim 5, wherein there are six 17-gauge catheters and wherein the predetermined distance of the catheters extending outwardly from the distal end of the semi-rigid tube is at least 6 cm. long and the catheter tubes are attached to the soft sheet at least 1 cm. apart.

7. The apparatus of claim 1, wherein the soft sheet is made of plastic material.

8. A method for intraoperative internal placement of an afterloading catheter for post-operative radiotherapy using the apparatus of claim 1, comprising the steps of:
    (a) inserting the distal end of the apparatus into a body cavity;
    (b) unfurling the soft sheet; and
    (c) securing the soft sheet with sutures to the body cavity area intended for radiation therapy.

9. A method for intraoperative internal placement of an afterloading catheter for post-operative radiotherapy using the apparatus of claim 3, comprising the steps of:
    (a) inserting the distal end of the semi-rigid tube containing the plurality of catheters into a body cavity;
    (b) removing the stiff cover cap from around the furled soft sheet once the semi-rigid tube is in the body cavity;
    (c) unfurling the soft sheet; and
    (d) securing the soft sheet with sutures to the body cavity area intended for radiation therapy.

* * * * *